(12) United States Patent
Abdallah

(10) Patent No.: US 8,226,905 B2
(45) Date of Patent: Jul. 24, 2012

(54) BLOOD GLUCOSE MEASUREMENT DEVICE

(76) Inventor: Richard Abdallah, Coral Springs, FL (US)

( * ) Notice: Subject to any disclaimer, the term of this patent is extended or adjusted under 35 U.S.C. 154(b) by 66 days.

(21) Appl. No.: 12/708,254

(22) Filed: Feb. 18, 2010

(65) Prior Publication Data

US 2010/0210933 A1    Aug. 19, 2010

Related U.S. Application Data

(60) Provisional application No. 61/153,531, filed on Feb. 18, 2009.

(51) Int. Cl.
*G01N 33/00* (2006.01)
(52) U.S. Cl. ........ 422/404; 422/400; 422/420; 422/68.1
(58) Field of Classification Search .................. 422/400, 422/404, 420, 68.1
See application file for complete search history.

(56) References Cited

U.S. PATENT DOCUMENTS 4,731,726 A * 3/1988 Allen, III ...................... 600/300

* cited by examiner

*Primary Examiner* — Sam P Siefke
(74) *Attorney, Agent, or Firm* — Jerry D Haynes; The Law Office of Jerry D Haynes

(57) ABSTRACT

A blood glucose measuring system comprising: a computer mouse that transmits data to an associated computer; a LED display residing on the computer mouse; a blood glucose strip receiver residing on the computer mouse; a blood glucose measurement mechanism; and software residing on the associated computer which receives blood glucose data, where the software stores the data onto a database within the associated computer. In one exemplary embodiment, the mouse may include two actuation pads and Bluetooth technology to transmit data from the mouse to the associated computer. The LED display provided on the mouse displays the glucose results measured by the measurement means. The software residing on the associated computer tabulates the blood glucose measurements and stores the data in a predetermined format.

8 Claims, 1 Drawing Sheet

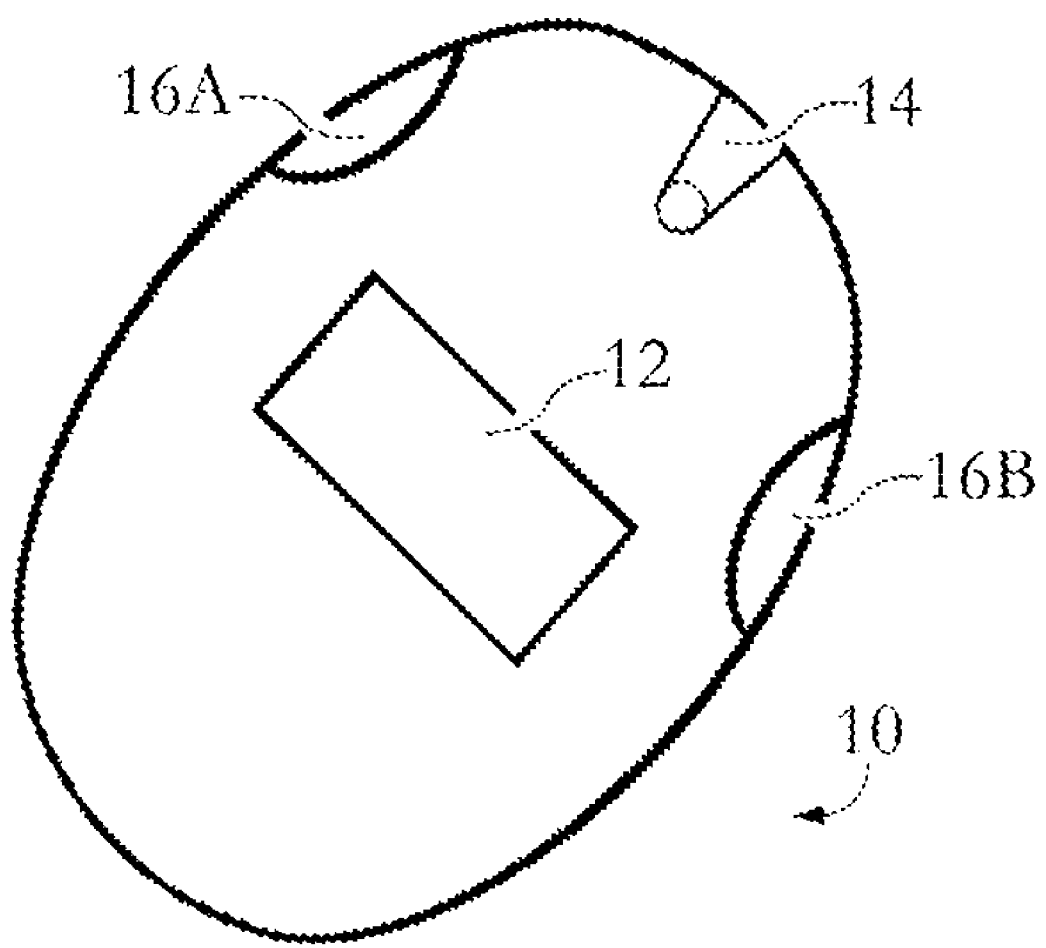

BLOOD GLUCOSE MEASUREMENT DEVICE

CROSS REFERENCE TO OTHER APPLICATIONS

This application claims priority to U.S. Provisional Application Ser. No. 61/153,531 filed on Feb. 18, 2009.

BACKGROUND OF THE INVENTION

1. Field of Invention

The present invention relates to a blood glucose-monitoring device which is incorporated into a wireless computer mouse.

2. Description of Related Art

Individuals suffering from diabetes used various testing devices in order to measure blood glucose levels within their blood stream on a daily basis. Typically a person who suffers from diabetes pricks their finger using a lancet. The lancet collects a droplet of blood which is then applied to a sensitive strip that is placed into a glucose measuring tool. Electronic devices are occasionally used to tabulate and track glucose measurements taken by diabetics where glucose measurements are loaded into a computer database via software. Other electronic devices store the glucose readings within a memory and transfer data to a database on a computer for storage. The electronic devices used to store glucose measurements have been known to connect directly to a computer or handheld device for storage of measurement data. An example of such a blood glucose tracking system is disclosed in U.S. Pat. No. 7,041,468.

Although electronic means for storage and transfer of blood glucose measurements are known, further developments in this area are conceivable and it would be advantageous to provide electronic measurement systems that incorporate other functions related to computing.

SUMMARY OF THE INVENTION

The present relates to a blood glucose measuring system comprising: a computer mouse that transmits data to an associated computer; a LED display residing on the computer mouse; a blood glucose strip receiver residing on the computer mouse; a blood glucose measurement means; and software residing on the associated computer which receives blood glucose data, where the software stores the data onto a database within the associated computer. In one exemplary embodiment, the mouse may include two actuation pads and Bluetooth technology to transmit data from the mouse to the associated computer. The LED display provided on the mouse displays the glucose results measured by the measurement means. The software residing on the associated computer tabulates the blood glucose measurements and stores the data in a predetermined format.

BRIEF DESCRIPTION OF DRAWINGS

FIG. 1 depicts an electronic blood glucose measuring and storage device according to the present invention.

DETAILED DESCRIPTION

In the following detailed description, reference is made to the accompanying drawings that show, by way of illustration, specific embodiments in which the invention may be practiced. These embodiments are described in sufficient detail to enable those skilled in the art to practice the invention.

The present invention provides a computer mouse that is capable of taking blood glucose measurements, providing a glucose measurement display and direct storage into a computer database. The present invention incorporates some known technology in a unique manner to address blood glucose measurements and the collection of data related thereto.

A blood glucose measurement mouse 10 as conceived by the present invention is shown in FIG. 1. The glucose mouse 10 includes a display screen 12 and a strip receiver 14. The glucose mouse 10 incorporates a blood glucose measurement device and may be used both to control a cursor on a computer screen and for the insertion of a blood glucose testing strip in order to obtain blood glucose measurements. The glucose mouse 10 includes two actuation pads 16A and 16B which provide the known computer interactive functions that a computer mouse typically addresses. The glucose mouse 10 as shown in FIG. 1 is a wireless mouse and therefore may include Bluetooth technology in order to transmit signals to a receiving device on a computer system. Although shown as a wireless mouse, the glucose mouse 10 may be configured in a hard-wired manner to a computer. The glucose mouse 10 has an LED display screen 12 that displays the glucose results from a diabetic glucose strip that is inserted into the strip receiver 14.

The glucose mouse 10 gives the user instantaneous readings of the blood glucose level and instantaneously transmits the data to software residing on an associated computer which tabulates the blood glucose measurements. The software, which functions with the glucose mouse 10, receives the data related to the blood glucose reading and stores the data in a predetermined format. The user then may retrieve the blood glucose readings that were taken for a period of time and provide the information to a medical care provider or transfer this data electronically to their medical providers. The alternatives provided by the glucose mouse 10 provide the user with an accurate and efficient means of recording and tabulating blood glucose readings.

The software that accompanies the glucose mouse 10 enables users to store their test results and these test results may be registered on an electronic calendar which records the date and time, and lists the existing insulin and data regarding appropriate dosage amounts needed to maintain sugar levels. The glucose mouse 10 may be designed for use with Accucheck testing strips that are currently used on the market and it provides the user with both the instantaneous information of the current level of the glucose and a complete readily accessible database of glucose readings over any period of time desired by the user. This unique incorporation of glucose testing technology with a computer mouse and software provides a streamline system to monitor blood glucose levels.

What is claimed is:

1. A blood glucose measuring system comprising:
   a. a computer mouse that transmits data to an associated computer, where said data includes controls for cursor movement on a computer screen for the associated computer and blood glucose data;
   b. a LED display residing on the computer mouse;
   c. a blood glucose strip receiver residing on the computer mouse;
   d. a blood glucose measurement means; and
   e. software residing on the associated computer which receives blood glucose data, where the software stores the data onto a database within the associated computer.

2. The blood glucose measuring system according to claim 1, where said mouse includes two actuation pads.

3. The blood glucose measuring system according to claim 1, where the mouse includes Bluetooth technology to transmit data from the mouse to the associated computer.

4. The blood glucose measuring system according to claim 1, where said LED display displays the glucose results measured by the measurement means.

5. The blood glucose measuring system according to claim 1, where the software residing on the associated computer tabulates the blood glucose measurements and stores the data in a predetermined format.

6. The blood glucose measuring system according to claim 5, where the predetermined format includes placement of the data on an electronic calendar that records the date and time of each glucose measurement.

7. The blood glucose measuring system according to claim 6, where the predetermined format includes a listing of the existing insulin and data regarding appropriate dosage amounts needed to maintain sugar levels.

8. The blood glucose measuring system according to claim 1, where the blood glucose strip receiver residing on the computer mouse is designed to use Accucheck testing strips.

* * * * *